(12) United States Patent
Wahlbom et al.

(10) Patent No.: US 7,381,551 B2
(45) Date of Patent: Jun. 3, 2008

(54) *SACCHAROMYCES CEREVISIAE* MUTANT

(75) Inventors: Fredrik Wahlbom, Malmö (SE);
Bärbel Hanh-Hägerdal, Lund (SE);
Leif Jönsson, Karlstad (SE)

(73) Assignee: Forskarpatent I Syd AB, Lund (SE)

( * ) Notice: Subject to any disclaimer, the term of this patent is extended or adjusted under 35 U.S.C. 154(b) by 550 days.

(21) Appl. No.: 10/946,654

(22) Filed: Sep. 20, 2004

(65) Prior Publication Data
US 2005/0208636 A1    Sep. 22, 2005

Related U.S. Application Data

(63) Continuation of application No. PCT/SE03/00397, filed on Mar. 11, 2003.

(30) Foreign Application Priority Data
Mar. 19, 2002    (SE) ................................ 0200855

(51) Int. Cl.
*C12P 7/06*    (2006.01)
*C12N 1/00*    (2006.01)
*C12N 15/74*    (2006.01)

(52) U.S. Cl. ................ 435/161; 435/254.21; 435/471; 435/483

(58) Field of Classification Search .................... None
See application file for complete search history.

(56) References Cited

U.S. PATENT DOCUMENTS 5,789,210 A * 8/1998 Ho et al. .................... 435/163

FOREIGN PATENT DOCUMENTS

WO    WO 01/88094 A1 * 11/2001
WO    WO/0188094    11/2001

OTHER PUBLICATIONS

Wahlbom et al., Molecular analysis of a *Saccharomyces cerevisiae* mutant with improved ability to utilize xylose shows enhanced expression of proteins involved in transport, initial xylose metabolism, and the pentose phosphate pathway. Appl. Environ. Microbiol., Feb. 2003, vol. 69 (2): 740-746. (In IDS).*

Leibowitz et al., pet18: A chromosomal gene required for cell growth and for maintenance of mitochondrial DNA and the killer plasmid of yeast. Molec. gen. Genet., 1978, vol. 165: 115-121.*

Jeffries et al., Genetic engineering for improved xylose fermentation by yeasts. Advances in Biochemical Engineering/Biotechnology, 1999, vol. 65: 117-161. Book Chapter, publishers, Springer-Verlag, Berlin Heidelberg.*

Whisstock et al., Prediction of protein function from protein sequence and structure. Q Rev. Biophys., 2003, vol. 36 (3): 307-340.*

Applied and Environmental Microbiology, vol. 69, No. 2, Feb. 2003, Wahlbom et al., "Molecular Analysis of a *Saccharomyces cerevisiae* Mutant with Improved Ability To Utilize Xylose Shows Enhanced Expression of Proteins Involved in Transport, Initial Xylose Metabolism, and the Pentose Phosphate Pathway", pp. 740-746.

FEMS Yeast Research, vol. 2, 2002, Johansson et al., "The non-oxidative pentose phosphate pathway controls the fermentation rate of xylulose but not of xylose in *Saccharomyces cerevisiae* TMB3001", pp. 277-282.

Applied and Environmental Microbiology, vol. 61, No. 12, Dec. 1995, Walfridsson et al., "Xylose-Metabolizing *Saccharomyces cerevisiae* Strains Overexpressing the TKL1 and TAL1 Genes Encoding the Pentose Phosphate Pathway Enzymes Transketolase and Transaldolase", pp. 4184-4190.

* cited by examiner

*Primary Examiner*—Tekchand Saidha
*Assistant Examiner*—Ganapathirama Raghu
(74) *Attorney, Agent, or Firm*—Gauthier & Connors LLP

(57) ABSTRACT

The present invention relates to a method for improved ethanol production from xylose utilizing strain of *Saccharomyces cerevisiae* comprising genes for overexpression of xylose reductase, xylitol dehydrogenase and xylulokinase, wherein in addition to said genes, one or more specific genes of a defined group is overexpressed, and/or one or more genes of a defined group is deleted.

3 Claims, No Drawings

SEQUENCE LISTING

<160> NUMBER OF SEQ ID NOS: 2

<210> SEQ ID NO 1
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
gcactagtat gagctgtacc actgataagt ta                                     32

<210> SEQ ID NO 2
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
gcgaattctt aggcgttgta acaagattca aaa                                    33

SACCHAROMYCES CEREVISIAE MUTANT

This application claims priority under 35 U.S.C. 119(a)-(d). This application is a CON of PCT/SE03/00397 filed on Mar. 11, 2003 and claims the priority date of foreign application: SWEDEN 0200855-5 filed on Mar. 19, 2002.

DESCRIPTION

1. Technical Field

The present invention relates a method for improving ethanol production from xylose utilising strain of Saccharomyces cerevisiae comprising genes for overexpression of xylose reductase, xylitol dehydrogenase and xylulokinase.

2. Background of the Invention

Xylose is one of the most abundant building blocks in hemicellulose (Sjöström, 1993) and thus represents a large fraction of all organic carbon. Saccharomyces cerevisiae, the preferred organism for industrial ethanol production, cannot utilise xylose. However, this trait is necessary to make the production of fuel ethanol from xylose-rich lignocellulose cost-effective (von Sivers and Zacchi, 1996).

Recently, a polyploid strain of S. cerevisiae (van der Westhuizen and Pretorius, 1992) was transformed with the genes coding for xylose reductase (XR) and xylitol dehydrogenase (XDH) from the xylose-utilising yeast Pichia stipitis as well as with the S. cerevisiae gene encoding xylulokinase (XK) (Wahlbom, et al., 2002). The resulting transformant, S. cerevisiae TMB 3399, had a maximum specific growth rate of 0.025 $h^{-1}$ when cultivated in a defined mineral medium supplemented with xylose. Chemical mutagenesis using ethyl methanesulphonate (EMS) generated mutants with improved growth rate and xylose utilisation. The best mutant selected was designated S. cerevisiae TMB 3400 and showed a more than five-fold increased growth rate, 0.14 $h^{-1}$, when cultivated under the same conditions as S. cerevisiae TMB 3399. The mutant, S. cerevisiae TMB 3400, also showed lower xylitol production than S. cerevisiae TMB 3399 when the strains were cultivated on xylose under oxygen-limited and anaerobic conditions.

Micro-array technology permits the quantification of genome-wide mRNA expression (Wodicka, et al., 1997). The technique offers the possibility to characterise differences in transcription level as a function of strain difference or cultivation condition. In S. cerevisiae micro-array technology has, among other things, been used to compare the mRNA expression during growth under aerobic and anaerobic conditions (ter Linde, et al., 1999) and during a shift from growth on a fermentable carbon source to growth on a non-fermentable carbon source (Kuhn, et al., 2001).

DETAILED DESCRIPTION OF THE PRESENT INVENTION

It has now been found possible to produce an improved ethanol producing strain of Saccharomyces cerevisiae utilising xylose, which strain besides genes for overexpression of xylose reductase, xylitol dehydrogenase and xyluloki nase, comprises in addition to said genes, one or more genes of the group consisting of PET18 (YCR020C), HXT5 (YHR096c), GAL2 (YLR081w), SOL3 (YHR163w), GND1 (YHR183w), TAL1 (YLR354c), TKL1 (YPR074c), PCK1 (YKR097w), ICL1 (YER065c), MLS1 (YNL117w), GAL1 (YBR020w), GAL7 (YBR018c), GAL10 (YBR019c) and CAT8 (YMR280c), wherein open reading frames are given in brackets, are overexpressed.

In accordance with a preferred embodiment one or more of the genes selected from the group consisting of TEC1 (YBR083w), ARR1 (YPR199c), MIG1 (YGL035c), MIG2 (YGL209w), wherein open reading frames are given in brackets, are deleted.

In accordance with a further preferred embodiment one or more genes is overexpressed, and one or more genes is deleted.

With the aim of identifying genes beneficial for growth on xylose, micro-array technology was used to compare mRNA expression in S. cerevisiae TMB 3399 and TMB 3400 as well as their growth on glucose and xylose. S. cerevisiae TMB 3399 was cultivated in batch and chemostat cultures at a dilution rate of 0.1 $h^{-1}$ in a defined mineral medium supplemented with either glucose or a mixture of glucose and xylose. S. cerevisiae TMB 3400 was cultivated under the same conditions and additionally using a feed containing only xylose. At steady state, samples were withdrawn for micro-array analysis, analysis of XR, XDH and XK activity as well as substrate consumption and product formation.

Materials and Methods

Strains, Medium and Cultivation Conditions

S. cerevisiae TMB 3399 and S. cerevisiae TMB 3400 were stored at −80° C. and streaked on YPD plates one day prior to inoculation of precultures. A defined mineral medium including vitamins and trace elements was used in all fermentation experiments (Verduyn, et al., 1990). The carbon and energy source consisted of 10 g $l^{-1}$ glucose, 10 g $l^{-1}$ glucose plus 10 g $l^{-1}$ xylose or 20 g $l^{-1}$ xylose. Antifoam (Dow Corning® Antifoam RD Emulsion, BDH Laboratory Supplies, Poole, England) was added to a concentration of 0.5 ml per liter.

The precultures consisted of 100 ml medium containing 10 g $l^{-1}$ glucose in 1000 ml baffled shake-flasks and were incubated at 30° C. and 140 rpm in an orbital incubator (Gallenkamp INR-200, Leicester, UK). The precultures used for cultivation of S. cerevisiae TMB 3400 on pure xylose were cultivated under the same conditions but with 20 g $l^{-1}$ xylose as the carbon source. The bioreactors were inoculated with 20 mg $l^{-1}$ of cells harvested in the late exponential phase.

Batch and chemostat fermentation was conducted at 30° C. in 2 l Biostat® A bioreactors (B. Braun Biotech International, Melsungen, Germany). The working volume of the bioreactors was 1200 ml and the pH was automatically maintained at 5.5 with 3 M NaOH. The air flow rate of 1 l $min^{-1}$ was controlled by mass flowmeters (Bronkhorst HI-TECH, Ruurlo, The Netherlands) and the dissolved oxygen tension was at least 30% of the maximum. Duplicate fermentation experiments were performed for each feed composition.

Sampling, Preparation of cRNA, Micro-array Analysis and Analysis of Substrates and Products Sampling Steady-state conditions were assumed when the carbon dioxide evolution, oxygen consumption and $OD_{620}$ had remained constant for three consecutive fermentor volumes. This occurred at least 6 fermentor volumes after feed initialisation or feed change. Samples were then withdrawn for micro-array analysis (2×50 ml), enzymatic assays (50 ml) and for the analysis of dry weight, substrate consumption and product formation (50 ml). The biomass concentrations were between 5 and 8 mg $ml^{-1}$ (Table 1).

Preparation of cRNA and Micro-array Analysis

Cells for micro-array analysis were kept on ice for 30 min. The cell samples were subsequently centrifuged at 5000 g and 4° C. for 5 min. The cells were then washed twice with ice-cold AE buffer (consisting of 50 nM sodium acetate, pH 5.2, and 10 mM EDTA). The cell pellets were frozen in liquid nitrogen and stored at −80° C. while awaiting further processing. Total RNA was isolated using the hot-phenol method (Schmitt, et al., 1990) and mRNA was purified using the Oligotex™ mRNA Mini Kit (Qiagen, Hilden, Germany). Synthesis of cDNA was performed using the Superscript Choice System (Gibco BRL Life Technologies, Gaithersburg, Md., USA) and a T7-(dT)24 oligonucleotide primer (Genset, Paris, France). In vitro transcription was carried out using the Enzo BioArray High Yield RNA Transcript Labeling Kit (Enzo Diagnostics, Farmingdale, N.Y., USA). The cRNA was fragmented and the hybridisation mixture prepared according to the recommendations of the manufacturer of the micro-arrays (Affymetrix, Santa Clara, Calif., USA). Hybridisation, washing, staining and scanning of the micro-arrays (GeneChip Yeast Genome S98 Arrays) were performed using a Hybridization Oven 320, a Fluidics Station 400 and a GeneArray Scanner (all from Affymetrix). Data were collected and processed using the Microarray Suite Software, version 4.0 (Affymetrix).

Enzymatic Analysis

Cells for enzymatic activity measurements were washed once with distilled water and treated with yeast protein extraction solution (Y-PER™, Pierce, Rockford, Ill., USA) for 20 min at room temperature. The mixture was centrifuged at 4° C. and 5000 rpm for 5 min and the supernatant was used for enzymatic assays. XR, XDH and XK were assayed as previously described (Eliasson, et al., 2000), but triethanolamine buffer at pH 7.0 was used instead of glycine buffer at pH 9.0 for the XDH assay, since the high pH of the glycine buffer caused precipitation of components in the extraction solution.

Analysis of Substrate and Products

Glucose, xylose, xylitol, succinate, glycerol, acetate and ethanol were analysed by HPLC as has been described previously (Wahlbom, et al., 2001). The composition of the outgoing gas was continuously monitored with a Carbon Dioxide and Oxygen Monitor Type 1308 (Brüel & Kjfr, Copenhagen, Denmark) (Christensen, et al., 1995) using photoacoustic and magnetoacoustic detection for $CO_2$ and $O_2$, respectively. The cell dry weight was determined by filtering a known volume of the culture broth through a 0.45 µm Supor membrane (Gelman Sciences, Ann Arbor, Mich., USA). After washing with three volumes of double-distilled water and drying in a microwave oven for 15 min at 900 W, the filter was weighed. The cell dry weight was determined in triplicate.

Construction of Strains with Open Reading Frame YCR020c Overexpressed and Deleted Strains and Vectors for Cloning and Expression E. coli DH5α (Life Technologies, Rockville, Md., USA) was used for cloning procedures. The p426ADH (ATCC 87377) multicopy vector (Mumberg, et al., 1995) was used to overexpress the open reading frame (ORF) YCR020c. This vector contains the β-lactamase gene, the URA3 selection marker and an ADH1 promoter and CYC1 terminator. The integrative plasmid YIpXR/XDH/XK (Eliasson, et al., 2000) carries three genes encoding enzymes involved in xylose utilisation, namely XR, XDH and XK, the β-lactamase gene and an HIS3 marker gene. The strains S. cerevisiae Y00000 [BY4741; MAT a; his3-Δ1; leu2Δ0; met15Δ0] and S. cerevisiae Y03500 [BY4741; MAT a; his3-Δ1; leu2Δ0; met15Δ0; YCR020c::kanMX4] were obtained from Euroscarf (Frankfurt, Germany).

Construction of Xylose-utilising Strains with Overexpression and Deletion of WCR020c All enzymes used for cloning and restriction analysis were obtained from Fermentas (Vilnius, Lithuania) unless stated otherwise. Standard techniques were used for cloning, transformation and analysis (Ausubel, 1987). Chromosomal DNA from S. cerevisiae TMB 3400 was prepared using the Easy-DNA kit (Invitrogen, Carlsbad, Calif., USA) and was used as the template for PCR amplification of the ORF YCR020C. The PCR product was obtained using the upstream primer 5'-GC<u>ACTAGT</u>A TGA GCT GTA CCA CTG ATA AGT TA-3' (SEQ ID NO: 1) in combination with the downstream primer 5'-GC<u>GAATTC</u>T TAG GCG TTG TAA CAA GAT TCA AAA-3' (SEQ ID NO: 2). The start codon is indicated in bold and the restriction sites for BcuI (SpeI) (upstream primer) and EcoRI (downstream primer) are underlined. The concentrations of nucleotides, Pwo DNA polymerase, primers and $Mg^{2+}$ ions were those recommended by the supplier (Roche, Mannheim, Germany). The PCR was performed in a GeneAmp PCR System 9700 (Perkin Elmer Corp., Norwalk, Conn., USA) and the conditions employed were as follows: 94° C. for 1 min, 55° C. for 30 s and 72° C. for 1 min (10 cycles), 94° C. for 1 min, 61° C. for 30 s and 72° C. for 1.5 min (15 cycles), 94° C. for 1 min, 61° C. for 30 s and 72° C. for 2.5 min (10 cycles). The PCR product was purified with the QiaQuick kit (Qiagen, Hilden, Germany) and together with the vector p426 ADH it was cleaved with BcuI and EcoRI and ligated with T4 DNA ligase to form the plasmid pFW5.

S. cerevisiae TMB 3151 was created by integrating the YIpXR/XDH/XK plasmid (Eliasson, et al., 2000), linearised by digestion with PstI, into the HIS3 locus of the laboratory strain S. cerevisiae CEN.PK 113-11C [MAT a his3-Δ1 ura3-52]. S. cerevisiae TMB 3151 was transformed with the plasmids p426ADH and pFW5 resulting in the strains S. cerevisiae TMB 3152 and TMB 3155, respectively.

S. cerevisiae Y00000 and S. cerevisiae Y03500 were transformed with the YIpXR/XDH/XK plasmid in the same way as S. cerevisiae CEN.PK 113-11C, and were named S. cerevisiae TMB 3159 and TMB 3160, respectively.

Cultivation of Strains with YCR020c Overexpressed and Deleted

The recombinant strains S. cerevisiae TMB 3152, 3155, 3159 and 3160 were cultivated using the same medium as described above. One-liter shake-flasks containing 100 ml medium supplemented with 20 g $l^{-1}$ glucose or 10 g $l^{-1}$ ethanol as well as 250-ml shake-flasks containing 25 ml medium supplemented with 10 g $l^{-1}$ xylulose or 20 g $l^{-1}$ xylose were incubated at 30° C. in a rotary shaker. The growth rate was determined by measuring the optical density (OD) at 620 nm. Duplicate cultivation experiments were performed for each substrate and strain.

Results

Chemostat Cultivation of S. cerevisiae TMB 3399 and TMB 3400

S. cerevisiae TMB 3399 and TMB 3400 were first cultivated in a batch, where the carbon source consisted of 10 g $l^{-1}$ glucose, and from which the maximum specific growth rates were determined to be 0.44±0.006 $h^{-1}$ for both strains. At the late exponential phase, chemostat cultivation was initiated by feeding with a defined mineral medium, first supplemented with glucose (10 g $l^{-1}$) and, six fermentor volumes later, with a mixture of 10 g l$^{-1}$ glucose plus 10 g l$^{-1}$ xylose. Since only S. cerevisiae TMB 3400 and not S. cerevisiae TMB 3399 shows a maximum specific growth rate exceeding 0.1 h$^{-1}$ on xylose, which is required to prevent wash-out, only S. cerevisiae TMB 3400 was cultivated in chemostat with xylose as sole carbon source. S. cerevisiae TMB 3400 was first cultivated in a batch supplemented with 20 g l$^{-1}$ xylose, and thereafter a feed of 20 g l$^{-1}$ xylose was added.

The biomass yield was around 0.47 g biomass (g consumed carbohydrate)$^{-1}$ for both strains during growth on glucose and glucose plus xylose, while it decreased to 0.43 g biomass (g consumed carbohydrate)$^{-1}$ for S. cerevisiae TMB 3400 during growth on xylose only (Table 1). The specific glucose consumption was 247 and 231 mg (g biomass h)$^{-1}$ for S. cerevisiae TMB 3399 and S. cerevisiae TMB 3400, respectively, when cultivated on glucose only. When grown on a mixture of glucose and xylose, S. cerevisiae TMB 3399 gave higher residual glucose and xylose concentrations, 0.09 and 4.6 g l$^{-1}$, respectively, then S. cerevisiae TMB 3400, which gave no detectable glucose and only 2.9 g l$^{-1}$ xylose. The specific glucose consumption was higher for S. cerevisiae TMB 3399; 160 mg (g biomass h)$^{-1}$ compared with 142 mg (g biomass h)$^{-1}$ for S. cerevisiae TMB 3400. The reverse was true for the specific xylose consumption; 85 mg (g biomass h)$^{-1}$ for S. cerevisiae TMB 3399 and 97 mg (g biomass h)$^{-1}$ for S. cerevisiae TMB 3400. Xylitol, 2.5 mg (g biomass h)$^{-1}$, was formed during cultivation of S. cerevisiae TMB 3399. During growth on xylose only, S. cerevisiae TMB 3400 consumed 12.3 g l$^{-1}$ of 20.8 g l$^{-1}$ in the feed and the specific xylose uptake, 254 mg (g biomass h)$^{-1}$, more than doubled compared with cultivation on the mixture of glucose and xylose. A $K_s$ value of 4.9 g l$^{-1}$, or 33 mM, was obtained by employing Monod kinetics (Nielsen and Villadsen, 1994) using D=0.1 h$^{-1}$, $D_{crit}$=0.14 h$^{-1}$ and s=12.3 g l$^{-1}$, S. cerevisiae TMB 3400 also produced a small amount of xylitol, 1 mg (g biomass h)$^{-1}$. The carbon balances closed within 94-103% for all fermentation experiments.

mRNA Expression Levels

The mRNA expression levels of the more than 6000 genes in the genome of S. cerevisiae were monitored simultaneously using DNA micro-arrays. In the present investigation, we chose to analyse mRNA expression levels of genes encoding sugar transporters and enzymes involved in xylose metabolism, the pentose phosphate pathway, glycolysis, gluconeogenesis and galactose metabolism (Table 2), as well as genes involved in regulation (Table 3). All microarray experiments were performed in duplicate, using cells from two independent fermentation experiments. In general, the mRNA expression was around 40-60% lower in cells grown on xylose than in cells grown on glucose or glucose plus xylose (Tables 2 and 3).

There are 20 hexose transporters in S. cerevisiae (Boles and Hollenberg, 1997), of which mRNA expression levels for HXT4, HXT5 and HXT7 together with galactose permease, GAL2, were monitored (Table 2). HXT5 was more highly expressed in S. cerevisiae TMB 3400 than in S. cerevisiae TMB 3399, both on glucose and on the mixture of glucose and xylose. The expression of GAL2 was about 70 times higher when xylose was the only sugar in the feed compared with the case when glucose also was present.

With regard to xylose metabolism, the heterologous genes encoding XR and XDH were not included in the analysis since they were cloned from P. stipitis and, hence, they are not represented on the S. cerevisiae DNA micro-arrays. The expression of S. cerevisiae genes encoding enzymes with XR (YHR104w) (Kuhn, et al., 1995) and XDH (YLR070c) (Richard, et al., 1999) activities was analysed. There was, however, no major difference in expression of these two genes when the recombinant and mutant strains were compared. The XKS1 gene encoding xylulokinase was expressed at about twice as high levels in S. cerevisiae TMB 3400 compared with TMB 3399. SOL3 and GND1, as well as TAL1 and TKL1, encoding enzymes in the oxidative and non-oxidative pentose phosphate pathway, respectively, were expressed at higher levels in S. cerevisiae TMB 3400 than in TMB 3399. Genes encoding phosphoenolpyruvate carboxykinase and the gluconeogenetic enzymes isocitrate lyase and malate synthetase, as well as genes involved in galactose metabolism, were upregulated in S. cerevisiae TMB 3400 during growth on xylose only.

Among the genes involved in regulation, notably YBR083W and YPR199C were expressed at lower levels in S. cerevisiae TMB 3400 than in TMB 3399 (Table 3). The PET18 gene (YCR020C), which encodes a transcription regulator, was expressed at high levels in S. cerevisiae TMB 3400 during growth on the mixture of glucose and xylose. When S. cerevisiae TMB 3400 was grown on xylose only, the expression of MIG1 and MIG2 was lower while the expression of CAT8 was higher.

Enzymatic Activities

The specific activities of enzymes involved in the initial xylose metabolism, XR, XDH and XK, are given in Table 4. All three enzymes display higher activities in S. cerevisiae TMB 3400 than in S. cerevisiae TMB 3399, regardless of whether the feed contained only glucose or glucose plus xylose. The specific activity determined in the cell extracts from xylose-grown S. cerevisiae TMB 3400 was very low for all three enzymes.

Characterisation of PET18

Among the genes encoding proteins involved in gene regulation that were differently expressed in S. cerevisiae TMB 3399 and its mutant S. cerevisiae TMB 3400 (Table 3), the effect of the transcription regulator encoded by PET18 on xylose utilisation was further investigated. Strains with overexpression and deletion of PET18 as well as control strains were developed and cultivated in shake-flasks with defined mineral medium supplemented with glucose, xylose, xylulose and ethanol (Table 5). The effect of PET18 on glucose and ethanol growth was negligible. The growth on xylulose was not significantly affected when PET18 was overexpressed, but deletion of the gene slightly improved the growth rate. Xylose growth was hampered by overexpression but did not change the performance of the strain in which PET18 was deleted.

Discussion

S. cerevisiae TMB 3399, transformed with the genes encoding XR, XDH and XK, showed a growth rate of 0.025 h$^{-1}$ (Wahlbom, et al., 2002) and it was subjected to chemical mutagenesis with EMS to further improve its ability to utilise xylose. The best-performing mutant, S. cerevisiae TMB 3400, showed a more than five-fold increase in maximum specific growth on xylose (0.14 h$^{-1}$) (Wahlbom, et al., 2002). Random mutagenesis combined with a good selection protocol generates strains displaying the characteristics selected for, whereas the site(s) of the mutation(s) remains unknown. In the present investigation, we report for the first time, the use of micro-array technology to characterise a recombinant strain of S. cerevisiae chemically mutated for better growth on a non-natural substrate. All micro-array experiments were performed in duplicate starting with independent fermentation experiments and the percentage error (difference from the mean as a fraction of the mean) was in general less than 15-20%. Thus, reproducible DNA microarray results were obtained for a diploid, industrial strain of S. cerevisiae.

In S. cerevisiae TMB 3400, the genes HXT5, encoding a hexose transporter, XKS1, encoding xylulokinase, SOL3 and GND1, coding for proteins in the oxidative pentose phosphate pathway, as well as, but to a lesser extent, TKL1 and TAL1 in the non-oxidative pentose phosphate pathway, were expressed at higher levels than in the parental strain S. cerevisiae TMB 3399. The higher expression of these genes could explain the improved growth rate on xylose of S. cerevisiae TMB 3400 as well as its higher xylose uptake from a feed containing a mixture of xylose and glucose. The HXT5 gene encodes a hexose transporter with moderate affinity for glucose (40 mM) (Diderich, et al., 2001). It has been reported to be abundant during slow growth on glucose and on growth on non-fermentable carbon sources, but in contrast to our results. It was suggested to be glucose repressed. The higher mRNA levels of XK in S. cerevisiae TMB 3400 is in agreement with a previous investigation of a S. cerevisiae strain mutated for improved xylose growth. The enzymatic activity of XK in the mutated S. cerevisiae IM2, with a maximum specific growth rate of $0.08\ h^{-1}$, was 60% higher than its parent S. cerevisiae H that has a maximum specific growth rate of $0.03\ h^{-1}$ (Tantirungkij, et al., 1994). Furthermore, XK activities were 5-10 higher in mutants of the natural xylose-utilising yeasts Pachysolen tannophilus (Lacke and Jeffries, 1986) and Candida utilis (McCracken and Gong, 1983) selected for improved utilisation of xylose and xylitol, respectively.

The higher expression of HXT5, XKS1, SOL3, GND1 as well as TKL1 and TAL1 in S. cerevisiae TMB3400 could be due to an altered expression of one or several transcription regulators acting on these genes. The transcription factors coded for by YCR020C, YBR083W and YPR199C were differently expressed in S. cerevisiae TMB 3400 and TMB 3399. The open reading frame YCR020C encodes the transcription factor Pet18p, which was expressed at higher levels in S. cerevisiae TMB 3400 than in S. cerevisiae TMB 3399 during growth on the mixture of glucose and xylose. The decision to investigate the influence of PET18 on xylose utilisation was based on its reported effect on carbon utilisation. Mutants defective in PET18 have been reported to be unable to grow on non-fermentable carbon sources (Winzeler, et al., 1998). However, we found that a strain in which PET18 was deleted was capable of growth on ethanol. Furthermore, xylose growth was unaffected by deleting as well as by overexpressing PET18. The transcription factors encoded by YBR083W and YPR199C deserve further attention and their effect on xylose utilisation in S. cerevisiae will be reported in a forthcoming publication.

The development of the superior xylose-utilising S. cerevisiae TMB 3400 allowed us to perform a physiological comparison as well as a comparison of mRNA expression levels between growth on xylose and glucose. The first chemostat cultivation of a recombinant S. cerevisiae strain on xylose as sole carbon source is presented here. S. cerevisiae TMB 3400 consumed about 40% of the xylose in the feed. This permitted us to determine the $K_s$ value for xylose (33 mM) which is approximately 60 times higher than the corresponding value reported for growth on glucose (0.55 mM) (Verduyn, et al., 1990). The biomass yield was lower on xylose than on glucose, so S. cerevisiae TMB 3400 can apparently not obtain as much energy from xylose as from glucose, which points towards a difference in the metabolism of these substrates. During growth on xylose, the gluconeogenetic gene encoding phosphoenolpyruvate carboxykinase, and the glyoxylate genes encoding isocitrate lyase and malate synthase were upregulated. When carbon is channelled through the glyoxylate shunt, ATP (GTP) is lost due to a reduced flux between succinyl CoA and succinate. A lower ATP yield may be responsible for the lower biomass yield of S. cerevisiae TMB 3400 on xylose compared with glucose. In a previous investigation, batch cultivation of S. cerevisiae TMB 3399 and 3400 showed biomass yields of 0.39 and 0.41 g biomass/g xylose, respectively (Wahlbom, et al., 2002). The fact that both the transformant S. cerevisiae TMB 3399 and the mutant S. cerevisiae TMB 3400 displayed similar biomass yields on xylose, indicates that the lower biomass yield on xylose is not due to a mutation. The genes encoding phosphoenolpyruvate carboxykinase and the glyoxylate genes encoding isocitrate lyase and malate synthase are upregulated by CAT8 (Caspary, et al., 1997; Randez-Gil, et al., 1997; Rahner, et al., 1999) which in turn is repressed by the glucose transcription regulator Mig1p (Hedges, et al., 1995). Our results show higher mRNA levels of CAT8 and lower expression of MIG1 during growth on xylose than on glucose.

MIG1 also regulates genes involved in galactose metabolism. The analysis of S. cerevisiae TMB 3400 showed that galactose permease, galactokinase, galactose 1-phosphate uridyl transferase and UDP-glucose 4-epimerase were expressed at higher levels during growth on only xylose compared with growth on glucose or the combination of glucose and xylose. In the presence of glucose, MIG1 causes repression of the transcription of genes involved in galactose metabolism (Nehlin, et al., 1991). However, galactose has been reported to be necessary for full initiation of transcription (Suzuki-Fujimoto, et al., 1996; Yano and Fukasawa, 1997) and it remains to be elucidated whether the increased expression of these genes in S. cerevisiae TMB 3400 is mediated by xylose or is due to a mutation.

Compared with the case when glucose was present in the medium, growth on xylose alone led to considerably lower mRNA expression levels for all genes except for phosphoenolpyruvate carboxykinase, isocitrate lyase, malate synthase, CAT8 and the genes in galactose metabolism. The in vitro activity of XR, which is under the control of an ADH promoter and the activities of XDH and XK, which are controlled by a PGK promoter, were also lower during xylose growth than glucose growth. Expression levels of alcohol dehydrogenase 1 (ADH) were 40% lower during xylose growth (data not shown). It has been demonstrated that the induction of glycolytic genes requires increased concentrations of metabolites in the early stages of glycolysis (Schaaff, et al., 1989; Müller, et al., 1995; Hauf, et al., 2000). These concentrations might be insufficient during xylose growth for full induction of glycolysis.

As a conclusion it can be stated that differences between the recombinant xylose-utilising Saccharomyces cerevisiae strain TMB 3399 and the mutant TMB 3400, derived from TMB 3399 and displaying improved ability to utilise xylose, were investigated using genome-wide expression analysis, physiological characterisation and biochemical assays. Samples for analysis were withdrawn from chemostat cultures. The characteristics for S. cerevisiae TMB 3399 and TMB 3400 grown on glucose and on a mixture of glucose and xylose, as well as for S. cerevisiae TMB 3400 grown on only xylose, were investigated. The strains were cultivated under chemostat conditions at a dilution rate of $0.1\ h^{-1}$ with feeds consisting of a defined mineral medium supplemented with 10 g l$^{-1}$ glucose, 10 g l$^{-1}$ glucose+10 g l$^{-1}$ xylose and for *S. cerevisiae* TMB 3400 20 g l$^{-1}$ xylose. *S. cerevisiae* TMB 3400 consumed 31% more xylose than *S. cerevisiae* TMB 3399 of a feed containing both glucose and xylose. The biomass yield for *S. cerevisiae* TMB 3400 was 0.46 g g$^{-1}$ on glucose and 0.43 g g$^{-1}$ on xylose. A $K_s$ value of 33 mM for xylose was obtained for *S. cerevisiae* TMB 3400. The percentage error was in general less than 15-20% between duplicate micro-array experiments originating from independent fermentation experiments. Micro-array analysis showed higher expression in *S. cerevisiae* TMB 3400 than in *S. cerevisiae* TMB 3399 for (i) HXT5, encoding a hexose transporter, (ii) XKS1, encoding xylulokinase, an enzyme involved in one of the initial steps of xylose utilisation, and (iii) SOL3, GND1, TAL1 and TKL1, encoding enzymes in the pentose phosphate pathway. In addition, the transcriptional regulators encoded by YCR020C, YBR083W and YPR199C were expressed differently in the two strains. Xylose utilisation was, however, not affected in strains in which YCR020C was overexpressed or deleted. The higher expression of XKS1 in *S. cerevisiae* TMB 3400 compared with TMB 3399 correlated with higher specific xylulokinase activity in cell extracts. The specific activity of xylose reductase and xylitol dehydrogenase was also higher for *S. cerevisiae* TMB 3400 than for TMB 3399, both on glucose and on the mixture of glucose and xylose.

TABLE 1

Feed concentrations, residual substrate concentrations and specific productivities from chemostat cultivation of *S. cerevisiae* TMB 3399 and *S. cerevisiae* TMB 3400 using glucose and xylose as carbon sources. (N.D. = Not detected)

| Strain | Feed concentration[a] Glucose | Feed concentration[a] Xylose | Residual concentration[a] Glucose | Residual concentration[a] Xylose | Biomass[a] X | Biomass yield[b] $Y_{sx}$ | Specific productivities[c] $q_{glucose}$ | Specific productivities[c] $q_{xylose}$ | Specific productivities[c] $q_{xylitol}$ | Specific productivities[c] $q_{co2}$ | C-balance[d] |
|---|---|---|---|---|---|---|---|---|---|---|---|
| *S. cerevisiae* TMB 3399 | 10.8 ± 0.2 | — | N.D. | — | 5.1 ± 0.2 | 0.48 ± 0.01 | −247 ± 3 | — | — | 143 ± 7 | 96 |
| *S. cerevisiae* TMB 3400 | 10.8 ± 0.2 | — | N.D. | — | 4.9 ± 0.2 | 0.46 ± 0.01 | −231 ± 6 | — | — | 136 ± 1 | 94 |
| *S. cerevisiae* TMB 3399 | 10.2 ± 0.1 | 10.0 ± 0.2 | 0.09 ± 0.06 | 4.6 ± 0.1 | 7.4 ± 0.1 | 0.48 ± 0.01 | −160 ± 1 | −85 ± 2 | 2.5 ± 0.5 | 150 ± 1 | 101 |
| *S. cerevisiae* TMB 3400 | 10.2 ± 0.1 | 10.0 ± 0.2 | N.D. | 2.9 ± 0.4 | 8.1 ± 0.4 | 0.47 ± 0.01 | −142 ± 3 | −97 ± 5 | N.D | 155 ± 3 | 103 |
| *S. cerevisiae* TMB 3400 | — | 20.8 ± 0.1 | — | 8.5 ± 0.12 | 5.4 ± 0.1 | 0.43 ± 0.01 | — | −254 ± 2 | 1 ± 0.1 | 163 ± 1 | 94 |

[a] g l$^{-1}$
[b] g biomass (g consumed carbohydrate)$^{-1}$
[c] i mg (g biomass h)$^{-1}$
[d] %

TABLE 2 mRNA expression levels In *S. cerevisiae* TMB 3399 and *S. cerevisiae* TMB 3400 for genes coding for transporters, enzymes involved in xylose metabolism, the pentose phosphate pathway, glycolysis, glyoxylate shunt, gluconeogenesis and galactose metabolism. The numbers are means and differences from the means of two independent fermentation experiments. Expressions that differ significantly are underlined and highlighted in bold face.

| | | | mRNA levels (Arbitrary units) | | | | |
|---|---|---|---|---|---|---|---|
| | | | Glucose feed | | Glucose + Xylose feed | | Xylose feed |
| ORF | Gene | Description | *S. cerevisiae* TMB 3399 | *S. cerevisiae* TMB 3400 | *S. cerevisiae* TMB 3399 | *S. cerevisiae* TMB 3400 | *S. cerevisiae* TMB 3400 |
| | | Hexose transporters | | | | | |
| YHR092C | HXT4 | High-affinity glucose transporter | 37 ± 11 | 25 ± 3 | 139 ± 104 | 55 ± 2 | 8 ± 0 |
| YHR096C | HXT5 | Hexose transporter | 634 ± 75 | 1,038 ± 176 | 654 ± 145 | 883 ± 157 | 1,314 ± 218 |
| YDR342C | HXT7 | Hexose transporter | 1967 ± 211 | 2097 ± 124 | 2476 ± 290 | 1981 ± 249 | 1,327 ± 36 |
| YLR081W | GAL2 | Galactose permease | 11 ± 3 | 6 ± 2 | 8 ± 5 | 8 ± 7 | 688 ± 19 |
| | | Xylose metabolism | | | | | |
| YHR104W | GRE3 | Aldo-keto-reductase | 160 ± 12 | 209 ± 18 | 209 ± 50 | 249 ± 14 | 306 ± 68 |
| YLR070C | | Strong similarity to sugar dehydrogenases | 55 ± 8 | 47 ± 5 | 60 ± 7 | 58 ± 12 | 52 ± 2 |
| YGR194C | XKS1 | Xylulokinase | 613 ± 87 | 1,278 ± 102 | 773 ± 160 | 1,207 ± 23 | 1,605 ± 176 |
| | | Pentose phosphate pathway | | | | | |
| YNL241C | ZWF1 | Glucose-6-phosphate dehydrogenase | 480 ± 69 | 400 ± 55 | 458 ± 69 | 471 ± 14 | 359 ± 32 |
| YHR163W | SOL3 | Shows similarity to glucose-6-phosphate dehydrogenase non-catalytic domains | 930 ± 169 | 1,577 ± 168 | 932 ± 95 | 1,824 ± 32 | 1,739 ± 168 |

TABLE 2-continued mRNA expression levels In *S. cerevisiae* TMB 3399 and *S. cerevisiae* TMB 3400 for genes coding for transporters, enzymes involved in xylose metabolism, the pentose phosphate pathway, glycolysis, glyoxylate shunt, gluconeogenesis and galactose metabolism. The numbers are means and differences from the means of two independent fermentation experiments. Expressions that differ significantly are underlined and highlighted in bold face.

| | | | mRNA levels (Arbitrary units) | | | | |
|---|---|---|---|---|---|---|---|
| | | | Glucose feed | | Glucose + Xylose feed | | Xylose feed |
| ORF | Gene | Description | *S. cerevisiae* TMB 3399 | *S. cerevisiae* TMB 3400 | *S. cerevisiae* TMB 3399 | *S. cerevisiae* TMB 3400 | *S. cerevisiae* TMB 3400 |
| YHR183W | GND1 | Phosphogluconate dehydrogenase (decarboxylating) | 1,664 ± 210 | 2,383 ± 104 | 1,804 ± 101 | 2,371 ± 114 | 2,396 ± 107 |
| YOR095C | RKI1 | Ribose-5-phosphate ketol-isomerase | 130 ± 4 | 207 ± 38 | 124 ± 18 | 129 ± 7 | 159 ± 27 |
| YJL121C | RPE1 | D-ribulose-5-phosphate 3-epimerase | 739 ± 13 | 707 ± 35 | 757 ± 181 | 683 ± 57 | 342 ± 38 |
| YLR354C | TAL1 | Transaldolase | 885 ± 66 | 1,124 ± 72 | 1,018 ± 129 | 1,209 ± 28 | 1,213 ± 13 |
| YPR074C | TKL1 | Transketolase 1 | 1,191 ± 34 | 1,595 ± 28 | 1,400 ± 63 | 1,646 ± 209 | 1,428 ± 67 |
| | | Glycolysis | | | | | |
| YFR053C | HXK1 | Hexokinase I (PI) (also called hexokinase A) | 1,250 ± 36 | 1,299 ± 261 | 1,440 ± 40 | 1,267 ± 194 | 700 ± 8 |
| YGL253W | HXK2 | Hexokinase II (PII) (also called hexokinase B) | 890 ± 36 | 782 ± 69 | 873 ± 149 | 877 ± 194 | 317 ± 23 |
| YDR516C | PGK | Strong similarity to glucokinase | 662 ± 44 | 629 ± 69 | 735 ± 32 | 785 ± 44 | 474 ± 100 |
| YBR196C | PGI | Glucose-6-phosphate isomerase | 1,349 ± 65 | 1,538 ± 114 | 1,640 ± 26 | 1,427 ± 97 | 1,400 ± 25 |
| YGR240C | PFK1 | Phosphofructokinase alpha subunit | 1,078 ± 56 | 1,157 ± 170 | 1,217 ± 89 | 1,085 ± 51 | 1,254 ± 49 |
| YKL060C | FBA1 | Aldolase | 3,244 ± 580 | 3,830 ± 206 | 4,123 ± 31 | 3,561 ± 550 | 4,194 ± 225 |
| YDR050C | TPI1 | Triosephosphate isomerase | 2743 ± 483 | 3196 ± 184 | 3324 ± 243 | 3370 ± 426 | 3452 ± 21 |
| YJL052W | TDH1 | Glyceraldehyde-3-phosphate dehydrogenase 1 | 2924 ± 600 | 3156 ± 74 | 3288 ± 30 | 3056 ± 516 | 3397 ± 225 |
| YJR009C | TDH2 | Glyceraldehyde 3-phosphate dehydrogenase | 3151 ± 466 | 3856 ± 76 | 4128 ± 11 | 3193 ± 623 | 3861 ± 115 |
| YGR192C | TDH3 | Glyceraldehyde-3-phosphate dehydrogenase 3 | 4058 ± 1066 | 4591 ± 250 | 4451 ± 45 | 4571 ± 749 | 4628 ± 553 |
| YCR012W | PGK | 3-Phosphoglycerate kinase | 2983 ± 507 | 3573 ± 123 | 3616 ± 58 | 3560 ± 507 | 3852 ± 217 |
| YKL152C | GPM1 | Phosphoglycerate mutase | 3206 ± 582 | 3371 ± 332 | 3796 ± 197 | 3248 ± 429 | 4037 ± 220 |
| YGR254W | ENO1 | Enolase I | 4015 ± 656 | 4410 ± 107 | 4498 ± 21 | 4278 ± 373 | 4152 ± 242 |
| YHR174W | ENO2 | Enolase | 2902 ± 191 | 3402 ± 102 | 3441 ± 264 | 2995 ± 369 | 2527 ± 71 |
| YAL038W | PYK1 | Pyruvate kinase 1 | 3051 ± 379 | 3235 ± 35 | 3617 ± 39 | 3307 ± 384 | 3479 ± 187 |
| | | Gluconeogenesis/Glyoxylate shunt | | | | | |
| YKR097W | PCK1 | Phosphoenolpyruvate carboxykinase | 381 ± 124 | 239 ± 94 | 252 ± 26 | 193 ± 77 | 694 ± 9 |
| YER065C | ICL1 | Isocitrate lyase | 454 ± 25 | 396 ± 54 | 473 ± 91 | 365 ± 140 | 1199 ± 62 |
| YNL117W | MLS1 | Carbon-catabolite-sensitive malate synthase | 163 ± 16 | 126 ± 4 | 132 ± 14 | 124 ± 32 | 184 ± 51 |
| | | Galactose metabolism | | | | | |
| YBR020W | GAL1 | Galactokinase | 6 ± 0 | 3 ± 0 | 4 ± 2 | 4 ± 1 | 160 ± 22 |
| YBR018C | GAL7 | Galactose-1-phosphate uridyl transferase | 8 ± 2 | 5 ± 0 | 9 ± 1 | 8 ± 1 | 477 ± 2 |
| YBR019C | GAL10 | UDP-glucose 4-epimerase | 11 ± 1 | 10 ± 1 | 14 ± 1 | 13 ± 0 | 333 ± 49 |

TABLE 3 mRNA levels of genes involved in regulation. Expressions that differ significantly are underlined and highlighted in bold face.

| | | | mRNA levels (Arbitrary units) | | | | |
|---|---|---|---|---|---|---|---|
| | | | Glucose feed | | Glucose + Xylose feed | | Xylose feed |
| ORF | Gene | Description | *S. cerevisiae* TMB 3399 | *S. cerevisiae* TMB 3400 | *S. cerevisiae* TMB 3399 | *S. cerevisiae* TMB 3400 | *S. cerevisiae* TMB 3400 |
| YBR083W | TEC1 | Transcription factor of the TEA/ATTS DNA-binding domain family, regulator of Ty1 expression | 140 ± 17 | 68 ± 15 | 175 ± 37 | 88 ± 31 | 107 ± 4 |
| YPR199C | ARR1 | Similar to transcriptional regulatory elements YAP1 and CAD1 | 160 ± 20 | 114 ± 12 | 166 ± 16 | 109 ± 2 | 120 ± 11 |

TABLE 3-continued mRNA levels of genes involved in regulation. Expressions that differ significantly are underlined and highlighted in bold face.

| | | | mRNA levels (Arbitrary units) | | | | |
|---|---|---|---|---|---|---|---|
| | | | Glucose feed | | Glucose + Xylose feed | | Xylose feed |
| ORF | Gene | Description | S. cerevisiae TMB 3399 | S. cerevisiae TMB 3400 | S. cerevisiae TMB 3399 | S. cerevisiae TMB 3400 | S. cerevisiae TMB 3400 |
| YCR020C | PET18 | Transcription regulator | 37 ± 1 | 41 ± 11 | 77 ± 32 | 204 ± 118 | 23 ± 11 |
| YDR477W | SNF1 | Protein serineVthreonine kinase | 94 ± 19 | 109 ± 1 | 64 ± 1 | 98 ± 1 | 116 ± 2 |
| YGL115W | SNF4 | Associates with Snf1p | 175 ± 25 | 206 ± 1 | 145 ± 3 | 179 ± 17 | 177 ± 1 |
| YGL035C | MIG1 | C2H2 zinc finger protein which resembles the mammalian Egr and Wilms tumour proteins | 14 ± 7 | 14 ± 3 | 23 ± 0 | 10 ± 9 | 6 ± 2 |
| YGL209W | MIG2 | Protein containing zinc fingers very similar to zinc fingers in Mig1P | 21 ± 1 | 16 ± 2 | 28 ± 1 | 22 ± 3 | 14 ± 6 |
| YMR280C | CAT8 | Zinc cluster protein involved in activating gluconeogenic genes\; related to Gal4p | 62 ± 1 | 58 ± 12 | 66 ± 9 | 48 ± 15 | 129 ± 23 |
| YPL248C | GAL4 | Zinc finger transcription factor of the Zn(2)-Cys(6) binuclear cluster domain type | 66 ± 2 | 59 ± 0 | 66 ± 0 | 74 ± 0 | 57 ± 2 |
| YML051W | GAL80 | Regulatory protein | 188 ± 12 | 147 ± 3 | 190 ± 27 | 174 ± 6 | 182 ± 17 |
| YDR009W | GAL3 | Galactokinase | 51 ± 17 | 44 ± 5 | 56 ± 9 | 39 ± 4 | 80 ± 11 |

TABLE 4

Enzymatic activities of xylose reductase (XR), xylitol dehydrogenase (XDH) and xylulokinase (XK) from chemostat cultivation of S. cerevisiae TMB 3399 and S. cerevisiae TMB 3400 on various feed concentrations of glucose and xylose.

| | Feed concentrations[a] | | Enzymatic activity[b] | | |
|---|---|---|---|---|---|
| Strain | Glucose | Xylose | XR | XDH | XK |
| S. cerevisiae TMB 3399 | 10.8 ± 0.2 | 0 | 0.20 ± 0.01 | 0.33 ± 0.02 | 0.44 ± 0.04 |
| S. cerevisiae TMB 3400 | 10.8 ± 0.2 | 0 | 0.50 ± 0.02 | 0.83 ± 0.1 | 0.60 ± 0.18 |
| S. cerevisiae TMB 3399 | 10.2 ± 0.1 | 10.0 ± 0.2 | 0.13 ± 0.01 | 0.36 ± 0.1 | 0.20 ± 0.08 |
| S. cerevisiae TMB 3400 | 10.2 ± 0.1 | 10.0 ± 0.2 | 0.32 ± 0.07 | 0.75 ± 0.25 | 0.27 ± 0.02 |
| S. cerevisiae TMB 3400 | 0 | 20.81 ± 0.1 | 0.08 ± 0.01 | 0.22 ± 0.07 | 0.07 ± 0.01 |

[a] g $l^{-1}$
[b] U (mg protein)$^{-1}$

TABLE 5

Maximum specific growth rates ($\mu^{max}$, $h^{-1}$) of S. cerevisiae TMB 3152, 3155, 3159 and 3160 grown in shake-flasks in a defined mineral medium supplemented with glucose (20 g $l^{-1}$), ethanol (10 g $l^{-1}$), xylulose (10 g $l^{-1}$) and xylose (10 g $l^{-1}$). The values are means of duplicate experiments where the relative error was less than 2%.

| | | Maximum specific growth rate | | | |
|---|---|---|---|---|---|
| Strain | Relevant genotype | Glucose | Xylose | Xylulose | Ethanol |
| S. cerevisiae TMB 3155 | Overexpressed YCR020c | 0.35 | 0.01 | 0.05 | 0.06 |
| S. cerevisiae TMB 3152 | Reference | 0.34 | 0.02 | 0.05 | 0.05 |
| S. cerevisiae TMB 3160 | Deleted YCR020c | 0.35 | 0.07 | 0.06 | 0.04 |
| S. cerevisiae TMB 3159 | Reference | 0.37 | 0.07 | 0.04 | 0.03 |

The invention claimed is:

1. A method for obtaining ethanol production wherein a xylose utilising *Saccharomyces cerevisiae* strain comprising expression of xylose reductase (XR) and xylitol dehydrogenase (XDH) encoding genes from *Pichia stipitis,* and a *Saccharomyces cerevisiae* gene encoding xylulokinase XK, has been subjected to chemical mutagenesis and selected for improved growth rate and xylose utilization is grown on xylose as a sole carbon source wherein in addition to said genes, the gene YCR020C coding for the transcription factor PET18, is overexpressed.

2. A method according to claim 1, wherein the gene YGL035c encoding a glucose transcription regulator MIG1 is deleted from *Saccharomyces cerevisiae* strain.

3. A method according to claim 1 or claim 2, wherein the *Saccharomyces cerevisiae* strain is TMB3400.

* * * * *